US00PP25568P2

(12) United States Plant Patent
van Aart

(10) Patent No.: US PP25,568 P2
(45) Date of Patent: May 19, 2015

(54) ***HIBISCUS* PLANT NAMED 'GANDINI SANTIAGO'**

(50) Latin Name: *Hibiscus syriacus*
Varietal Denomination: Gandini Santiago

(71) Applicant: Marinus Adrianus Cornelis van Aart, Oudenbosch (NL)

(72) Inventor: Marinus Adrianus Cornelis van Aart, Oudenbosch (NL)

(73) Assignee: Van Aart Boomkwekerijen, Oudenbosch (NL)

( * ) Notice: Subject to any disclaimer, the term of this patent is extended or adjusted under 35 U.S.C. 154(b) by 97 days.

(21) Appl. No.: 13/987,885

(22) Filed: Sep. 12, 2013

(51) Int. Cl.
*A01H 5/02* (2006.01)

(52) U.S. Cl.
USPC ..... Plt./257

(58) Field of Classification Search
CPC ..... A01H 5/02; A01H 5/00
USPC ..... Plt./257
See application file for complete search history.

*Primary Examiner* — Kent L Bell
(74) *Attorney, Agent, or Firm* — Penny J. Aguirre

(57) ABSTRACT

A new cultivar of *Hibiscus* plant named 'Grandini Santiago', that is characterized by its pyramidal plant habit, and by its sterile flowers that are pinkish violet in color with a large red-purple eye and double with the first flush of bloom and single on later blooms.

2 Drawing Sheets

Botanical classification: *Hibiscus syriacus.*
Cultivar designation: 'Gandini Santiago'.

BACKGROUND OF THE INVENTION

The present invention relates to a new and distinct cultivar of *Hibiscus* plant botanically known as *Hibiscus syriacus* 'Gandini Santiago' and will be referred to hereafter by its cultivar name, 'Gandini Santiago'. 'Gandini Santiago' is a new cultivar of hardy hibiscus grown for use as a landscape plant.

'Gandini Santiago' was discovered by the Inventor as a chance seedling in a nursery bed that had been planted with seeds of unnamed plants of *Hibiscus syriacus* in Girona, Spain in 2002.

Asexual propagation of the new cultivar was first accomplished by grafting in Oudenbosch, The Netherlands in September of 2009 under the direction of the Inventor. Asexual propagation by grafting and softwood stem cuttings has determined that the characteristics of the new cultivar are stable and are reproduced true to type in successive generations.

SUMMARY OF THE INVENTION

The following traits have been repeatedly observed and represent the characteristics of 'Gandini Santiago'. These attributes in combination distinguish 'Gandini Santiago' as a new and distinct cultivar of *Hibiscus.*

1. 'Gandini Santiago' exhibits a pyramidal plant habit.
2. 'Gandini Santiago' exhibits flowers that are pinkish violet in color with a large red-purple eye.
3. 'Gandini Santiago' exhibits flowers that are double with the first flush of bloom and single on later blooms.
4. 'Gandini Santiago' exhibits sterile flowers.

Typical plants of the species *Hibiscus syriacus*, differ from 'Gandini Santiago', most significantly in having flowers that are violet in color or violet with a small red eye. 'Gandini Santiago' can also be most closely compared to the cultivars 'Russian Violet' (not patented) and 'Pink Giant' (not patented). Both are similar to 'Gandini Santiago' in having flowers that have red centers. 'Russian Violet' differs from 'Gandini Santiago' in having flowers with a small red center and in lacking a pyramidal plant habit. 'Pink Giant' differs from 'Gandini Santiago' in having flowers that are pink in color with a deep red center, in lacking a pyramidal plant habit, and in producing fertile seed (not sterile).

BRIEF DESCRIPTION OF THE DRAWING

The accompanying colored photograph illustrates the overall appearance and distinct characteristics of the new *Hibiscus*. The photographs were taken of a two year-old plant of 'Gandini Santiago' as grown in a 3-liter container outdoors in Oudenbosch, The Netherlands.

The photograph in FIG. 1 provides a side view of 'Gandini Santiago' in bloom and illustrates its pyramidal plant habit.

Figure 1:
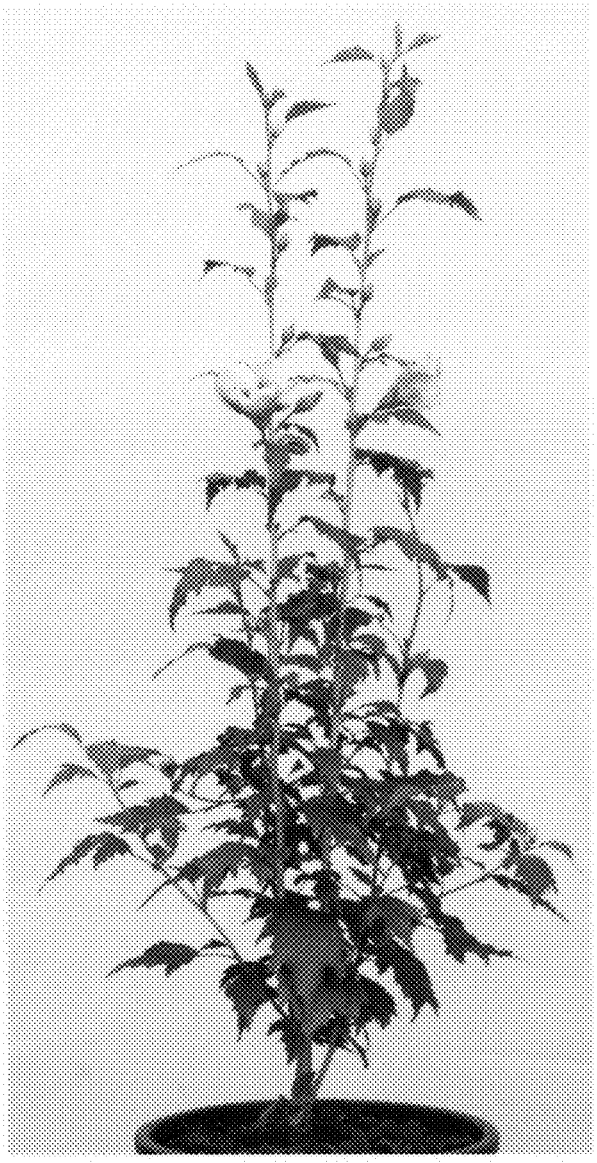
Figure 2:
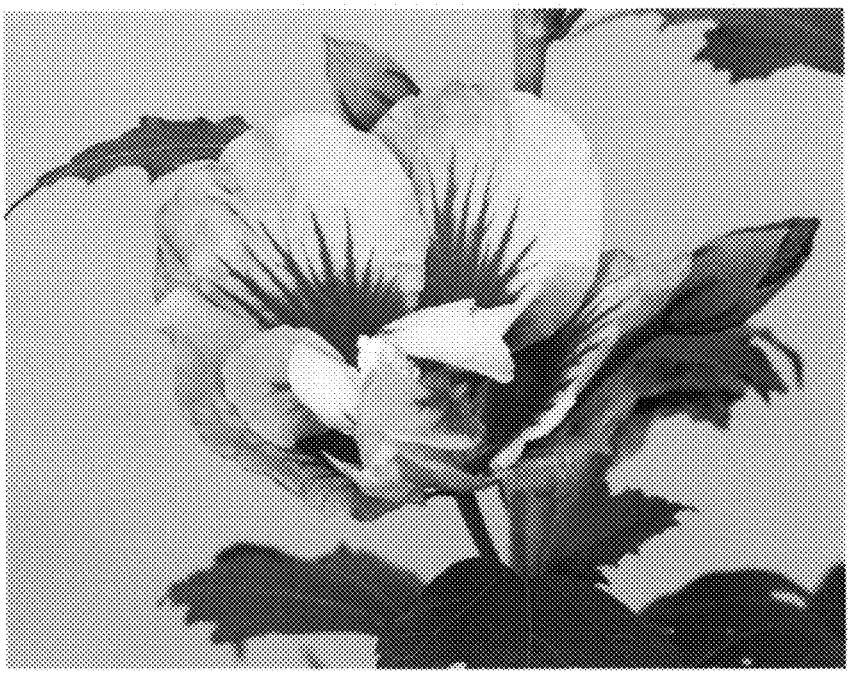

The photograph in FIG. 2 provides a close-up view of a flower of 'Gandini Santiago'.

Figure 3:
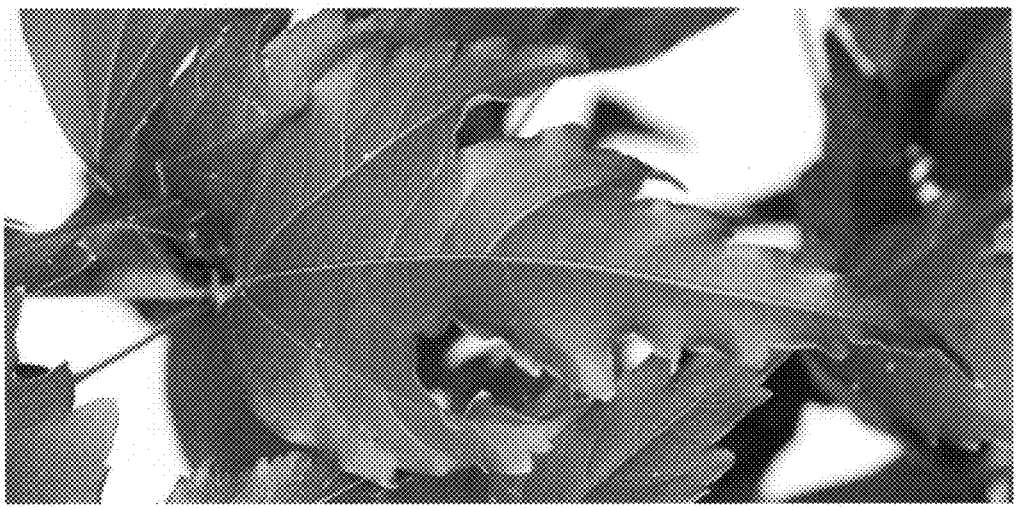

The photograph in FIG. 3 provides a close-up view of a leaf of 'Gandini Santiago'.

The colors in the photographs are as close as possible with the digital photography and printing techniques utilized and the color codes in the detailed botanical description accurately describe the new *Hibiscus.*

DETAILED BOTANICAL DESCRIPTION OF THE PLANT

The following is a detailed description of 2 year-old plants of the new cultivar as grown outdoors in 3-liter containers outdoors in Oudenbosch, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—August and September in The Netherlands.

*Plant habit*.—Herbaceous shrub.

*Height and spread*.—Reaches about 98 cm in height and 43.8 cm in spread as a 2 year-old plant in a container and 3 m in height and 80 cm in spread in the landscape when mature.

*Cold hardiness*.—At least in U.S.D.A. Zone 5.

*Diseases and pests*.—Not more susceptible or resistant to pests and diseases than other *Hibiscus syriacus* varieties.

*Root description*.—Fibrous roots.

*Propagation*.—Softwood stem cuttings.

*Growth rate*.—Vigorous.

Stem description:

*Shape*.—Round.

*Stem color*.—New growth; 143A, mature wood; 196D with lighter lenticels 196D.

*Stem size*.—An average of 47.4 cm in length and 5 mm in diameter.

*Stem surface*.—Smooth and covered with dense pubescence, consisting of very short hairs average of 0.2 mm and 157D.

*Stem aspect*.—Upright, in an average angle of 20°, varying between (0°=vertical) and 40°.

*Stem strength*.—Moderately strong.

*Branching*.—Moderately free branching, an average of 9 lateral branches.

*Internode*.—Average of 3.5 cm.

Foliage description:

*Leaf shape*.—Ovate to narrow rhomboidal, occasional with one lobe on each side.

*Leaf division*.—Simple.

*Leaf base*.—Obtuse.

*Leaf apex*.—Narrowly acute.

*Leaf venation*.—Pinnate, upper surface 137C in color, lower surface 144C in color.

*Leaf margins*.—Coarsely serrate.

*Leaf attachment*.—Petiolate.

*Leaf arrangement*.—Alternate.

*Leaf orientation*.—Held upright and slightly pendulant from mid section towards apex once matured.

*Leaf surface*.—Both sides dull, lower side sparsely covered with adpressed strigose hairs average of 1 mm in length and 156D.

*Leaf color*.—Young leaves upper surface; 143B, young leaves lower surface; 143C, mature leaves upper surface; 137B, mature leaves lower surface; 146B.

*Leaf size*.—Average of 10.4 cm in length, and 6.3 cm in width.

*Leaf quantity*.—About 14 leaves per lateral branch, 126 per plant.

*Petioles*.—Average of 4.2 cm in length, 1.5 mm in diameter, upper side 137C in color, lower side 144B in color.

Flower description:

*Inflorescence type*.—Flowers are solitary and double with the first flush of bloom and single on later blooms.

*Lastingness of flowers*.—About 5 days, self cleaning.

*Flower size*.—An average of 5.1 cm in depth and 12.4 cm in diameter.

*Flower fragrance*.—None.

*Flower shape*.—Rotate, typical Hibiscus shape.

*Flower number*.—Average of 8 per lateral stem.

*Flower aspect*.—Outward to slightly upright.

*Flower bud*.—Elliptic in shape, an average of 3 cm in length and 1.2 cm in width, color; 138B, top becoming N79B.

*Flower attachment*.—Petiolate.

*Petal number*.—5.

*Petal shape*.—Obcordate.

*Petal color*.—Upper surface when opening and fully opened; N80C to N80D, lower half and base of petal 59B to 60A, lower surface when opening and fully opened; N80B to N80C, base of petal 60C.

*Petal surface*.—Both surfaces smooth, upper side dull and glossy, lower side moderately glossy.

*Petal margins*.—Entire.

*Petal apex*.—Rounded.

*Petal size*.—Average of 6.1 cm in length and 5.1 cm in width.

*Petaloids* (*present on early double flowers*).—Small petaloids present at the base of the style, 1.7 cm in length and 4 mm in width, larger petaloids present along the style, 3.9 cm in length and 2 cm in width, average of 16, both sides of all are smooth and dull, narrow oblong to oblanceolate in shape, entire margins, color of young and mature upper and lower surfaces; 76B, base 63A.

*Sepal number*.—5.

*Sepal shape*.—Elliptic.

*Sepal margin*.—Entire.

*Sepal size*.—Average of 2 cm in length and 1 cm in width.

*Sepal aspect*.—Rotate, lower 50% fused.

*Sepal surface*.—Both sides dull and smooth.

*Sepal apex*.—Acute.

*Sepal base*.—Broad cuneate (fused).

*Sepal color*.—Young and mature upper surfaces; 145A, young lower surfaces; 138B, mature lower surfaces; 144B.

*Calyx*.—Rotate in shape, average of 1.9 cm in length and 2.4 cm in diameter.

*Peduncles*.—An average of 2.1 cm in length and 2 mm in diameter, moderately strong, average angle is 40° (0°=straight on top of lateral branch) and 138B to 138C in color.

*Pedicels*.—Not present, flowers emerge from terminals of stem and are solitary.

*Bracts*.—At the base of each flower is a ring of bracts adpressed against the sepals, average of 7, linear in shape, average of 1.8 cm in length and 1.5 mm in width and N137B in color.

Reproductive organs:

*Gynoecium*.—1 pistil, about 4.1 cm in length, stigmas; club-shaped, an average of 5 and 155A in color, style; 3.9 cm in length and NN155C in color, ovary; 150D in color and completely covered by the base of the style.

*Androecium*.—Stamens; average of 90 (less on double flowers), stamens are clustered and implanted in style, anthers; dorsifixed and orbicular in shape, 1.5 mm in length and 160D in color; filaments; 2 mm in length and 155A in color, pollen; abundant in quantity and 11C to 11D in color.

*Fruit/seeds*.—Sterile; fertile seeds are not produced.

It is claimed:

1. A new and distinct cultivar of *Hibiscus* plant named 'Gandini Santiago' as herein illustrated and described.

* * * * *